United States Patent [19]

Stearns

[11] Patent Number: 5,543,622
[45] Date of Patent: Aug. 6, 1996

[54] METHOD FOR DETERMINING DATA NORMALIZATION FACTORS FOR IMAGE RECONSTRUCTION

[75] Inventor: Charles W. Stearns, Milwaukee, Wis.

[73] Assignee: General Electric Company, Milwaukee, Wis.

[21] Appl. No.: 515,461

[22] Filed: Aug. 15, 1995

[51] Int. Cl.$^6$ .................................................. G01T 1/166
[52] U.S. Cl. ................................ 250/363.03; 250/363.09; 364/413.24
[58] Field of Search ......................... 250/363.03, 363.04, 250/363.09; 364/413.24; 378/901

[56] References Cited

U.S. PATENT DOCUMENTS

| | | | |
|---|---|---|---|
| 5,169,942 | 12/1992 | Johnson et al. | 536/122 |
| 5,230,831 | 7/1993 | Srivastava | 252/301.4 F |
| 5,241,181 | 8/1993 | Mertens et al. | 250/363.03 |
| 5,264,570 | 11/1993 | Johnson et al. | 536/122 |
| 5,272,343 | 12/1993 | Stearns | 250/363.03 |
| 5,272,344 | 12/1993 | Williams | 250/363.03 |
| 5,300,782 | 4/1994 | Johnston et al. | 250/363.03 |
| 5,323,007 | 6/1994 | Wernick et al. | 250/363.03 |
| 5,331,553 | 7/1994 | Muehllehner et al. | 364/413.24 |
| 5,378,893 | 1/1995 | Murray et al. | 250/363.03 |

OTHER PUBLICATIONS

"A Component Based Method for Normalization in Volume PET," M. E. Casey, H. Gadagkar, D. Newport, *Proceedings of the 1995 International Meeting on Fully Three-Dimensional Image Reconstruction in Radiology and Nuclear Medicine*, Jul. 4–6, 1995, pp. 67–71.

*Primary Examiner*—David P. Porta
*Assistant Examiner*—David Vernon Bruce
*Attorney, Agent, or Firm*—John S. Beulick; John H. Pilarski

[57] ABSTRACT

An algorithm for creating a normalization data array to use in generating a three-dimensional image is described. In one embodiment, the algorithm includes performing the steps of acquiring geometric factors from a two-dimensional normalization scan, determining the three-dimensional crystal sensitivities from a three-dimensional phantom acquisition scan, and using such geometric factors and crystal sensitivities, creating a three-dimensional normalization data array.

19 Claims, 2 Drawing Sheets

METHOD FOR DETERMINING DATA NORMALIZATION FACTORS FOR IMAGE RECONSTRUCTION

FIELD OF THE INVENTION

This invention relates generally to image generation and, more particularly, to determining normalization factors utilized in image reconstruction.

BACKGROUND OF THE INVENTION

Positron emission tomography (PET) scanners are utilized to generate images of, for example, portions of a patient's body. Positron attenuation data and/or annihilation events are utilized in generating such images. Positrons are positively charged electrons which are emitted by radionuclides that have been prepared using a cyclotron or other device. The radionuclides are employed as radioactive tracers called "radiopharmaceuticals" by incorporating them into substances, such as glucose or carbon dioxide. The radiopharmaceuticals are injected into the patient and become involved in such processes as blood flow, fatty acids, glucose metabolism, and synthesis.

Positrons are emitted as the radionuclides decay. The positrons travel a very short distance before encountering an electron, and when that occurs, the positron is annihilated and converted into two photons, or gamma rays. This annihilation event is characterized by two features which are directed in nearly opposite directions.

For detecting such events, the PET scanner has a ring of detectors that encircle the patient. The detectors comprise crystals, referred to as scintillators, to convert the energy of each 511 KeV photon into a flash of light that is sensed by a photomultiplier tube. Coincidence detection circuits connect to the detectors and record only those photons that are detected simultaneously by two detectors located on opposite sides of the patient. The number of such simultaneous events indicates the number of positron annihilations that occurred along a line joining the two opposing detectors.

During a scan, hundreds of million of events are detected and recorded to indicate the number of annihilation events along lines joining pairs of detectors in the ring. The collected data is used to reconstruct an image. Further details regard PET scanners are set forth in U.S. Pat. Nos. 5,378,893, 5,272,343, and 5,241,181, all of which are assigned to the present assignee.

With respect to data collected during a scan, such data typically is normalized prior to using such data to reconstruct an image. Known normalization methods for three-dimensional imaging, however, are based on coincidence sensitivity for two-dimensional imaging. In accordance with these known methods, coincidence sensitivity is the product of the single-crystal efficiencies of the two detectors forming the coincidence and a "geometric factor", which in two-dimensional imaging is assumed to be a function of line of response (LOR) radius only and not a function of LOR angle. To extend the method to three-dimensional imaging, it is known to use the square root of the product of the two single-ring geometric factors for the geometric factor of a cross-plane LOR.

These previous methods have several drawbacks which make them inappropriate for three-dimensional imaging on some scanners. For example, with two-dimensional scanning, septa (or detector shields) are utilized so that each detector only detects events on a specific plane. With known three-dimensional methods, the septa are removed. The sensitivity of each crystal with the septa out, however, is assumed to equal the sensitivity with septa in. In an ideal scanner, this assumption may be true since the septa and crystals are exactly in their desired locations. As crystals get smaller and septa thinner, however, minor positioning errors of 1 mm or less become a significant departure from the ideal case. In real applications, such positioning errors are likely to occur.

In addition, a rod source may be used for acquisition of two-dimensional normalization data. Particularly, the rod source has a generally known rate of radionuclide decay and is placed within the ring detector. Axial non-uniformity of the rod source makes it impossible to measure relative slice sensitivities. Since the two-dimensional normalization procedure is concerned only with sensitivity variations within the slice, such a limited sensitivity is acceptable for two-dimensional imaging. For three-dimensional imaging, however, relative slice sensitivities are important.

Further, although the geometric factor in two-dimensional imaging is assumed to be a function of the LOR radius only, in three-dimensional imaging, the geometric factor is not a simple function of LOR radius. Other effects may introduce a strong angular effect with some period greater than one row. Manufacturing variations in the scanner ring, such as variations in module-to-module spacing in the detector assembly, may also produce additional variations in system sensitivity which must be taken into account by the three-dimensional geometric factor.

Accordingly, it is desirable to provide a data normalization array for three-dimensional imaging which takes into account the fact that the septa and crystals may not be exactly located in their desired position and compensates for sensitivity variations within a slice as well as for relative slice sensitivities. It also is desirable to provide such an array which takes into account effects such as variations in module-to-module spacing.

SUMMARY OF THE INVENTION

These and other objects are attained by an algorithm for creating a normalization data array to use in generating a three-dimensional image. The algorithm, in one embodiment, includes performing the step of acquiring the geometric factors from two-dimensional normalization scan data. A three-dimensional phantom acquisition is then performed and the three-dimensional phantom data is used to determine the three-dimensional crystal sensitivities. Using such geometric factors and crystal sensitivities, the three-dimensional normalization data array is created.

More specifically, and in accordance with one embodiment, a scan is performed using a rod source. As a result of such scan, two-dimensional normalization scan $S(r,\phi,z)$ data is obtained. Then, the "high resolution" two-dimensional direct data planes are added together and an average direct data plane for the scanner is determined from the direct data planes. Each row of the average direct data plane is then divided by the expected sinogram profile for the rod source acquisition data. Geometric factors $g(r,\phi)$ are then determined from the average of every N'th sinogram row, where N is selected to equal 6, 12 or 336 based on the need for geometric modelling.

A three-dimensional phantom acquisition scan $S(u,v,\phi,\Theta)$ is then performed by limiting the range of the projection plane width u to cover the phantom only. The phantom data is divided by the geometric factor $g(u,\phi)$ to produce a sinogram $S'(u,v,\phi,\Theta)$. A mean sinogram row $\bar{S}'(u)$ is then determined from the arithmetic (or geometric) mean of the rows of sinogram $S'(u,v,\phi,\Theta)$. Sinogram $S'(u,v,\phi,\Theta)$ is then divided by the mean sinogram $\bar{S}'(u)$ to produce a sinogram $S''(u,v,\phi,\Theta)$. A crystal-averaging scheme can then be performed on $S''(u,v,\phi,\Theta)$ to produce a crystal efficiency array $e(X,Z)$. The three-dimensional normalization data array $N(u,v,\phi,\Theta)$ is then defined as $1/[g(u,\phi)e(X_1Z_1)e(X_2Z_2)]$.

The normalization data array algorithm described above takes into account, in creating the array, the fact that the septa and crystals may not be exactly located in their desired positions and compensates for sensitivity variations within a slice as well as for relative slice sensitivities. The algorithm also takes into account effects such as fishnet artifacts and variations in module-to-module spacing. As a result, the three-dimensional normalization data array created using the present algorithm facilitates reconstruction of a better three-dimensional image.

DETAILED DESCRIPTION OF THE DRAWINGS

Figure 1:
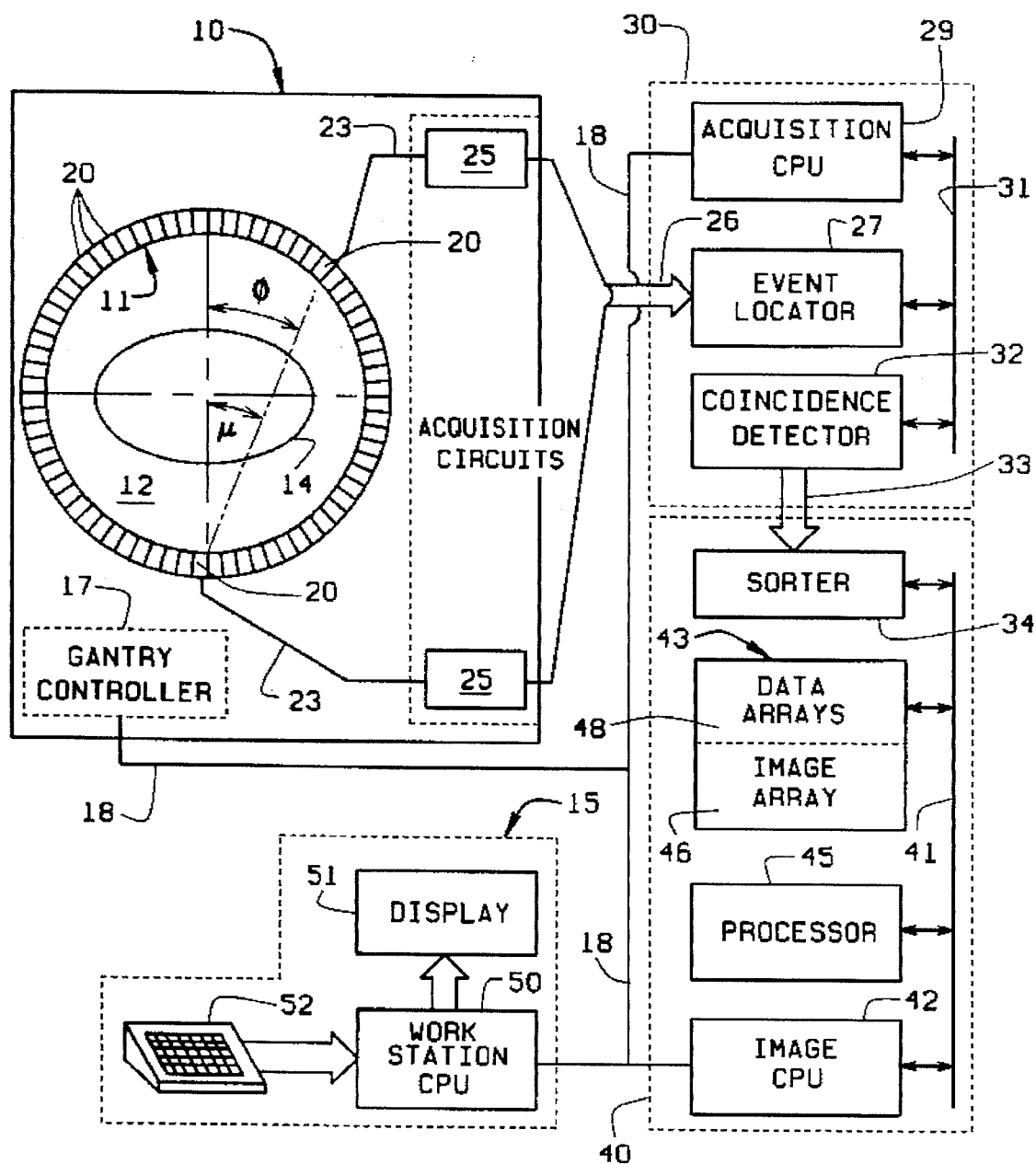
FIG. 1 is a schematic diagram of a PET scanner system.

Referring particularly to FIG. 1, a PET scanner system includes a gantry 10 which supports a detector ring assembly 11 about a central opening, or bore 12. A patient 14 is positioned on a motorized table (not shown) in front of gantry 10 and in alignment with the central axis of bore 12. A table moves patient 14 into bore 12 in response to commands received from an operator work station 15. A gantry controller 17 is mounted within gantry 10 and is responsive to commands received on a serial communications link 18 to operate gantry 10.

Detector ring assembly 11 is comprised of one hundred and twelve radiation detector units 20, for example. Each radiation detector unit 20 includes a set of scintillator crystals arranged in a matrix that is disposed in front of four photomultiplier tubes. Each photomultiplier tube produces an analog signal on line 23 when a scintillation event occurs. A set of acquisition circuits 25 are mounted within gantry 10 to receive these signals and produce digital signals indicating the event coordinates (x,y) and the total energy. The digital signals are transmitted through a cable 26 to an event locator circuit 27 housed in a separate cabinet. Each acquisition circuit 25 also produces an event detection pulse which indicates the exact moment the scintillation event took place.

Event locator circuits 27 form part of a data acquisition processor 30 which periodically samples the signals produced by acquisition circuits 25. Processor 30 has an acquisition CPU 29 that controls communications on a backplane bus 31 and on network 18. Event locator circuits 27 assemble the information regarding each valid event into a set of digital numbers that indicate precisely when the event took place and the position of the scintillator crystal which detected the event. This event data packet is conveyed to a coincidence detector 32 which is also pan of data acquisition processor 30.

Coincidence detector 32 accepts the event data packets from event locators 27 and determines if any two of them are in coincidence. Coincidence is determined by a number of factors. First, the time markers in each event data packet must be within a predetermined time period, e.g., 12.5 nanoseconds, of each other, and second, the locations indicated by the two event data packets must lie on a straight line which passes through the field of view in the scanner bore 12. Events which cannot be paired are discarded, but coincident event pairs are located and recorded as a coincidence data packet that is conveyed through a serial link 33 to a sorter 34.

Sorter 34 forms part of an image reconstruction processor 40. Sorter 34 counts all events occurring along each projection ray and organizes them into a two dimensional dam, or sinogram, array 48 which is stored in a memory module 43. The image reconstruction processor 40 also includes an image CPU 42 that controls a backplane bus 41 and links it to local area network 18. An array processor 45 also connects to backplane bus 41 and reconstructs images from data arrays 48. A resulting image array 46 is stored in memory module 43 and is output by image CPU 42 to operator work station 15.

Operator work station 15 includes a CPU 50, a CRT display 51 and a keyboard 52. CPU 50 connects to local area network 18 and scans keyboard 52 for input information. Through keyboard 52 and associated control panel switches, the operator can control the calibration of the PET scanner, its configuration, and the positioning of the patient for a scan. Similarly, the operator can control the display of the resulting image on CRT display 51 and perform image enhancement functions using programs executed by work station CPU 50.

Figure 2:
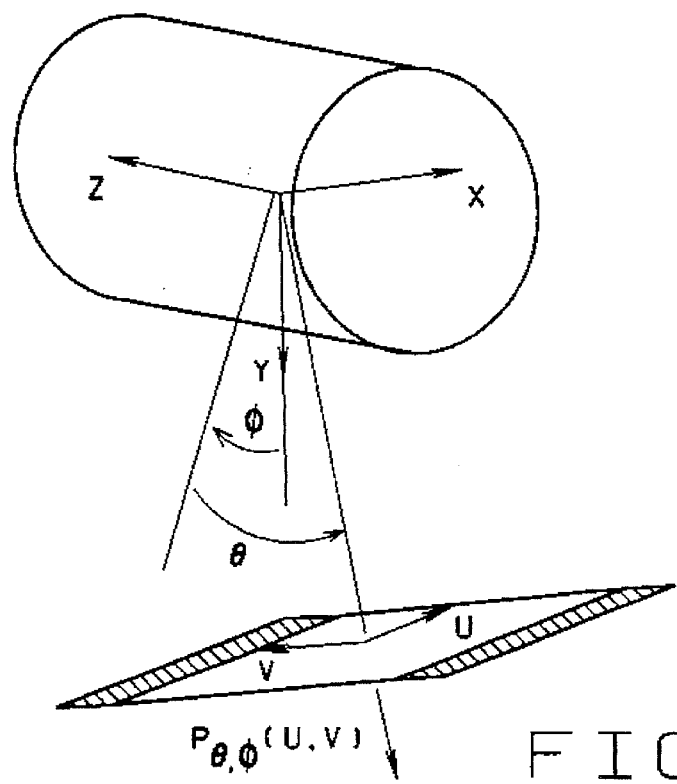
FIG. 2 illustrates volumetric measurements made by a PET scanner.

FIG. 2 illustrates an image volume and a projection plane. As shown in FIG. 2, and with respect to generating image array 46, the volumetric (three-dimensional) measurement of annihilation events within a PET scanner is accomplished by collecting projection planes $P_{\Theta,\phi}(u,v)$ of the events at each transaxial angle $\phi$ and a set of axial angles $\Theta$. The collected data is stored in data, or sinogram, arrays 48.

Once the data is collected and stored as described above, processor 45 then performs a normalization operation, as well as other operations, on data arrays 48. The normalized data is then stored in image array 46. When the image is desired to be displayed on display 51, image CPU 42 retrieves the image array 46 for display.

Figure 3:
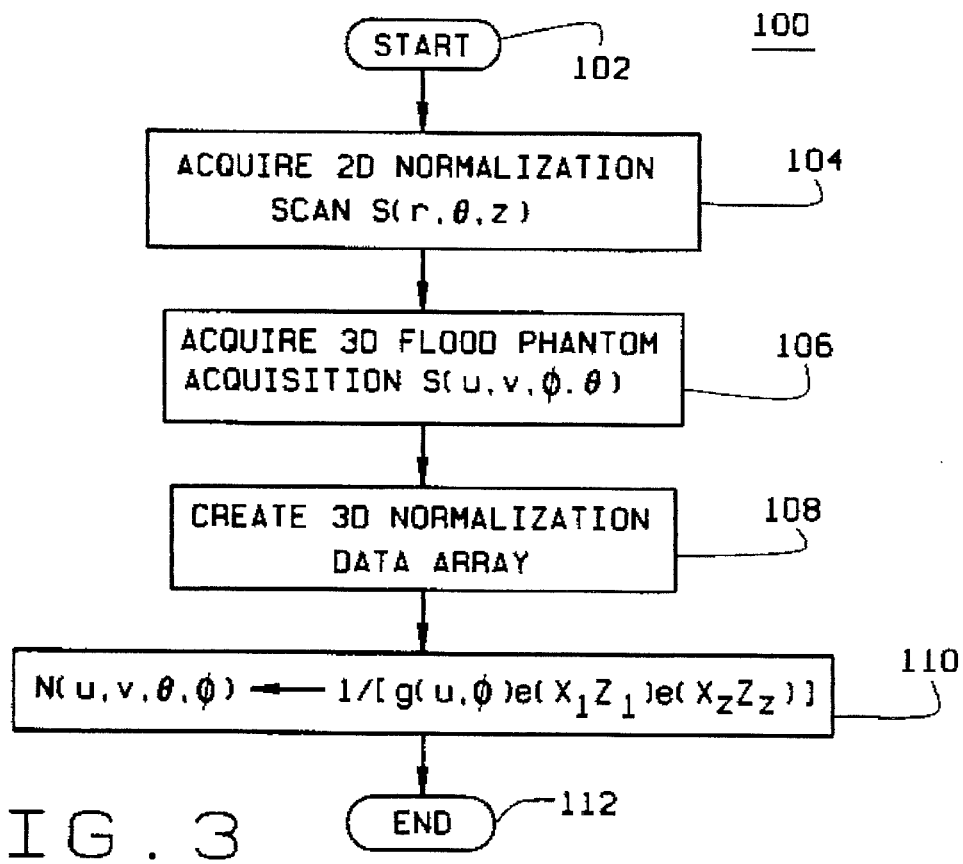
FIG. 3 is a flow chart illustrating a sequence of process steps in accordance with one embodiment of the present invention.

Referring now to FIG. 3, a sequence of process steps 100 in accordance with one embodiment of the present algorithm is illustrated. Process steps 100 would be performed, for example, by processor 45 on data arrays 48 as part of the image reconstruction process. In accordance with process steps 100 illustrated in FIG. 3, and once operations start 102, two-dimensional normalization scan $S(r,\phi,z)$ data is acquired 104. Such data is acquired, for example, by performing a scan using a rod source.

High resolution direct data planes are then obtained. If, for example, a detector is formed of eighteen rings of crystals, eighteen "high resolution" direct data planes for each ring are obtained by utilizing, for each ring, only coincidences detected by two crystals in the same plane. The high resolution data planes for each ring are then added together and divided by eighteen to provide an average direct data plane for the scanner. Each row of the average direct data plane is then divided by the expected sinogram profile for the rod source.

The geometric factors $g(r,\phi)$ are then determined from the average of every N'th sinogram row, where N is selected to be equal to an integral factor of the number of crystals in the sinogram array. For example, if a detector has six hundred and seventy two crystals, then the number of crystals in the sinogram array is three hundred and thirty six. In this example, N would be selected to equal, for example, 6, 12, 336 or some other integral factor of 336. For this specific example, N is set to equal 6. Rather than using an average of every N'th sinogram row, the geometric factors $g(r,\phi)$ could alternatively be determined from the geometric mean. A deadtime correction also could be performed on the geometric factors $g(r,\phi)$.

Three-dimensional phantom acquisition scan $S(u,v,\phi,\Theta)$ data is then acquired 106. In one embodiment, step 106 is performed by limiting the range of the projection plane width u to cover the phantom only. The phantom scan $S(u,v,\phi,\Theta)$ data is divided by the geometric factor $g(u,\phi)$ to produce a sinogram $S'(u,v,\phi,\Theta)$. A mean sinogram row $\overline{S}'(u)$ is determined from the arithmetic or geometric mean of the rows of sinogram $S'(u,v,\phi,\Theta)$, and sinogram $S'(u,v,\phi,\Theta)$ is divided by the mean sinogram $\overline{S}'(u)$ to produce a sinogram $S''(u,v,\phi,\Theta)$. A crystal-averaging scheme can then be performed on $S''(u,v,\phi,\Theta)$ to produce a crystal efficiency array $e(X,Z)$. Crystal-averaging schemes are well-known and described, for example, by Chesler and Stearns, IEEE Trans. Nucl. Sci., Vol. 37(2), pgs. 768–772.

The three-dimensional normalization data array is created 108 from the acquired two-dimensional normalization scan and the three-dimensional phantom data. More specifically, the normalization data array $N(u,v,\phi,\Theta)$ is defined as $1/[g(u,\phi)e(X_1Z_1)e(X_2Z_2)]$.

Normalized data array $N(u,v,\phi,\Theta)$ is used, for example, after performing a patient scan. Particularly, the measured scan data is multiplied by normalization data array $N(u,v,\phi,\Theta)$ to normalize the measured scan data. Other correction algorithms such as artifact correction algorithms, can also be performed as part of the three-dimensional image reconstruction process.

The normalization data array algorithm described above takes into account, in creating the normalization array, the fact that the septa and crystals may not be exactly located in their desired positions and compensates for sensitivity variations within a slice as well as for relative slice sensitivities. The algorithm also takes into account effects such as fishnet artifacts and variations in module-to-module spacing. As a result, the normalization data array $N(u,v,\phi,\Theta)$ created using the present algorithm facilitates reconstruction of a better image.

Since the geometric factors should not change significantly over time, the two-dimensional normalization scan to determine the geometric factors can be performed relatively infrequently. The three-dimensional phantom acquisition scan and creation of an updated three-dimensional normalization data array $N(u,v,\phi,\Theta)$ based on the phantom acquisition scan should be performed more often to estimate the faster-changing single crystal efficiencies.

From the preceding description of the present invention, it is evident that the objects of the invention are attained. Although the invention has been described and illustrated in detail, it is to be clearly understood that the same is intended by way of illustration and example only and is not be taken by way of limitation. Accordingly, the spirit and scope of the invention are to be limited only by the terms of the appended claims.

What is claimed is:

1. A method for creating a data normalization array for use in normalizing data acquired from a positron emission tomograph scan from a scanner to be used in generating a three-dimensional image, said method comprising the steps of:

acquiring two-dimensional normalization scan $S(r,\phi,z)$ data;

acquiring three-dimensional phantom scan $S(u,v,\phi,\Theta)$ data; and creating the three-dimensional normalization data array $N(u,v,\phi,\Theta)$ from the two-dimensional normalization scan $S(r,\phi,z)$ data and the three-dimensional phantom scan $S(u,v,\phi,\Theta)$ data.

2. A method in accordance with claim 1 wherein after acquiring the two-dimensional normalization scan $S(r,\phi,z)$ data, said method further comprises the steps of:

adding together direct data planes of the scan $S(r,\phi,z)$ data;

determining the average direct data plane for the scanner; and dividing each row of the average direct data plane by an expected sinogram profile of a rod source.

3. A method in accordance with claim 2 wherein said method further comprises the steps of:

determining geometric factors $g(r,\phi)$.

4. A method in accordance with claim 3 wherein the geometric factors $g(r,\phi)$ are determined from an average of every N'th sinogram row, where N is selected.

5. A method in accordance with claim 4 wherein N is selected to be equal to 6, 12 or 336.

6. A method in accordance with claim 3 wherein the geometric factors $g(r,\phi)$ are determined from a geometric mean.

7. A method in accordance with claim 3 wherein said method further comprises the step of:

performing a deadtime correction on the geometric factors $g(r,\phi)$.

8. A method in accordance with claim 1 wherein the three-dimensional phantom acquisition scan $S(u,v,\phi,\Theta)$ data is acquired by limiting the range of the projection plane width u to cover the phantom only and said method further comprises the steps of:

limiting the range of the projection plane width u to cover the phantom only;

dividing the phantom data $S(u,v,\phi,\Theta)$ by a geometric factor $g(u,\phi)$ to produce a sinogram $S'(u,v,\phi,\Theta)$;

determining a mean sinogram row $\overline{S}'(u)$ from the mean of the rows of sinogram $S'(u,v,\phi,\Theta)$;

dividing sinogram $S'(u,v,\phi,\Theta)$ by the mean sinogram $\overline{S}'(u)$ to produce a sinogram $S''(u,v,\phi,\Theta)$; and performing a crystal-averaging scheme on sinogram $S''(u,v,\phi,\Theta)$ to produce a crystal efficiency array $e(X,Z)$.

9. A method in accordance with claim 1 wherein the three-dimensional normalization data array $N(u,v,\phi,\Theta)$ is equal to $1/[g(u,\phi)e(X_1Z_1)e(X_2Z_2)]$ where $g(u,\phi)$ are geometric factors and $e(X_1Z_1)e(X_2Z_2)$ are representative of crystal efficiency.

10. A system for creating a data normalization array for use in normalizing data acquired from a positron emission tomograph scan from a scanner to be used in generating a three-dimensional image, said system comprising:

memory storage for storing two-dimensional normalization scan $S(r,\phi,z)$ data and three-dimensional phantom scan $S(u,v,\phi,\Theta)$ data; and a processor programmed to create a three-dimensional normalization data array $N(u,v,\phi,\Theta)$ from the two-dimensional normalization scan $S(r,\phi,z)$ data and the three-dimensional phantom scan $S(u,v,\phi,\Theta)$ data.

11. A system in accordance with claim 10 wherein said system processes the two-dimensional normalization scan $S(r,\phi,z)$ data by:

adding together direct data planes obtained from a scan performed using a rod source;

determining an average direct data plane for the scanner; and dividing each row of the average direct data plane by the expected sinogram profile of the rod source.

12. A system in accordance with claim 10 wherein geometric factors $g(r,\phi)$ are determined by said system from the two-dimensional normalization scan $S(r,\phi,z)$ data.

13. A system in accordance with claim 10 wherein the three-dimensional phantom acquisition scan $S(u,v,\phi,\Theta)$ data is acquired by limiting the range of the projection plane width u to cover the phantom only and a crystal efficiency array $e(X,Z)$ is generated by said system by:

dividing the phantom data by a geometric factor $g(u,\phi)$ to produce a sinogram $S'(u,v,\phi,\Theta)$;

determining a mean sinogram row $\overline{S}'(u)$ from a mean of the rows of sinogram $S'(u,v,\phi,\Theta)$;

dividing sinogram $S'(u,v,\phi,\Theta)$ by the mean sinogram $\overline{S}'(u)$ to produce a sinogram $S''(u,v,\phi,\Theta)$; and performing a crystal-averaging scheme on sinogram $S''(u,v,\phi,\Theta)$ to generate the crystal efficiency array $e(X,Z)$.

14. A system in accordance with claim 10 wherein the three-dimensional normalization data array $N(u,v,\phi,\Theta)$ is equal to $1/[g(u,\phi)e(X_1Z_1)e(X_2Z_2)]$ where $g(u,\phi)$ are geometric factors and $e(X_1Z_1)e(X_2Z_2)$ are representative of crystal efficiency.

15. A processor programmed for creating a data normalization array for use in normalizing data acquired from a positron emission tomograph scan to be used in generating a three-dimensional image, a memory storage being coupled to said processor for storing two-dimensional normalization scan $S(r,\phi,z)$ data and three-dimensional phantom scan $S(u,v,\phi,\Theta)$ data, said processor programmed to create a three-dimensional normalization data array $N(u,v,\phi,\Theta)$ from the two-dimensional normalization scan $S(r,\phi,z)$ data and the three-dimensional phantom scan $S(u,v,\phi,\Theta)$ data.

16. A processor in accordance with claim 15 wherein said processor processes the two-dimensional normalization scan $S(r,\phi,z)$ data by:

adding together direct data planes obtained from a scan performed using a rod source;

determining an average direct data plane for the scanner; and dividing each row of the average direct data plane by the expected sinogram profile of the rod source.

17. A processor in accordance with claim 15 wherein geometric factors $g(r,\phi)$ are determined by said processor from the two-dimensional normalization scan $S(r,\phi,z)$ data.

18. A processor in accordance with claim 15 wherein the three-dimensional phantom acquisition scan $S(u,v,\phi,\Theta)$ data is acquired by limiting the range of the projection plane width u to cover the phantom only and a crystal efficiency array $e(X,Z)$ is generated by said processor by:

dividing the phantom data by a geometric factor $g(u,\phi)$ to produce a sinogram $S'(u,v,\phi,\Theta)$;

determining a mean sinogram row $\overline{S}'(u)$ from a mean of the rows of sinogram $S'(u,v,\phi,\Theta)$;

dividing sinogram $S'(u,v,\phi,\Theta)$ by the mean sinogram $\overline{S}'(u)$ to produce a sinogram $S''(u,v,\phi,\Theta)$; and performing a crystal-averaging scheme on sinogram $S''(u,v,\phi,\Theta)$ to produce a crystal efficiency array $e(X,Z)$.

19. A processor in accordance with claim 15 wherein the three-dimensional normalization data array $N(u,v,\phi,\Theta)$ is equal to $1/[g(u,\phi)e(X_1Z_1)e(X_2Z_2)]$ where $g(u,\phi)$ are geometric factors and $e(X_1Z_1)e(X_2Z_2)$ are representative of crystal efficiency.

\* \* \* \* \*